United States Patent [19]

Miller

[11] 4,037,461
[45] July 26, 1977

[54] PROBE AND METHOD OF MAKING THE SAME

[75] Inventor: Charles Eveleigh Miller, Boulder, Colo.

[73] Assignee: International Telephone and Telegraph Corporation, New York, N.Y.

[21] Appl. No.: 711,739

[22] Filed: Aug. 5, 1976

[51] Int. Cl.² .............................................. G01N 9/00
[52] U.S. Cl. ................................................. 73/32 A
[58] Field of Search ...................... 73/32 A, 505, 70.2; 310/25

[56] References Cited

U.S. PATENT DOCUMENTS

| 2,432,424 | 12/1947 | Hyland et al. | 310/25 X |
| 2,504,719 | 4/1950 | Neilson | 310/25 |
| 3,174,331 | 3/1965 | Doherty et al. | 73/70.2 |
| 3,339,400 | 9/1967 | Banks | 73/32 A |
| 3,683,213 | 8/1972 | Staudte | 310/25 X |

Primary Examiner—James J. Gill
Attorney, Agent, or Firm—A. Donald Stolzy

[57] ABSTRACT

Vibration densitometer probes having vanes with central weights notched to vibrate at the same frequency when immersed in a fluid at the same density.

3 Claims, 5 Drawing Figures

PROBE AND METHOD OF MAKING THE SAME

BACKGROUND OF THE INVENTION

This invention relates to systems for producing output signals of a magnitude directly proportional to density.

In the past, vibration densitometers had to be individually calibrated for the same or different fluids. This added to the time required for and expense of their manufacture.

SUMMARY OF THE INVENTION

In accordance with the probe and method of the present invention, the above-described and other disadvantages of the prior art are overcome by making the resonant frequencies of manufactured probes uniform.

The above-described and other advantages of the present invention will be better understood from the following detailed description when considered in connection with the accompanying drawings.

BRIEF DESCRIPTION OF THE DRAWINGS

In the drawings, which are to be regarded as merely illustrative.

DESCRIPTION OF THE PREFERRED EMBODIMENT

Figure 1:
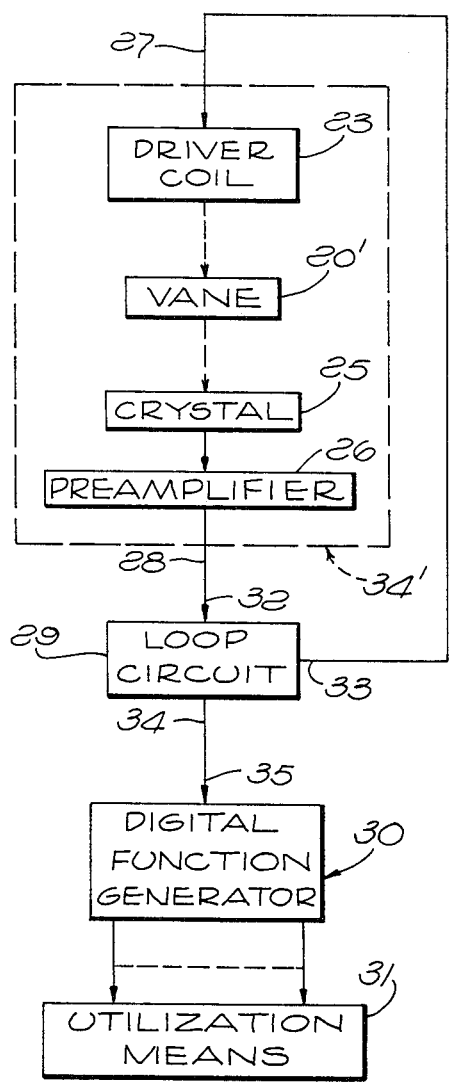
FIG. 1 is a block diagram of a densitometer constructed in accordance with the present invention.

In the drawings, in FIG. 1, a vibration densitometer probe is indicated at 34' having a driver coil 23, a vane 20', a piezoelectric crystal 25 and a preamplifier 26.

Probe 34' has an input lead 27 and an output lead 28.

Other blocks shown in FIG. 1 are a loop circuit 29, a digital function generator 30 and utilization means 31. Loop circuit 29 has an input lead 32 and output leads 33 and 34. Digital function generator 30 has an input lead 35 connected from loop circuit output lead 34. The output of digital function generator 30 is connected to utilization means 31.

The output lead 28 of probe 34' is connected to the input lead 32 of loop circuit 29. The input lead 27 of probe 34' is connected from the output lead 33 of loop circuit 29. Probe 34' and loop circuit 29 form a closed loop electromechanical oscillator. Vane 20' is submerged in a fluid. The density of the fluid is a function of the frequency at which vane 20' vibrates.

Digital function generator 30 may have its input lead 35 connected from lead 33 or at other points in loop circuit 29. Loop circuit 29 impresses a square wave voltage on input lead 35 of digital function generator 30 having a mark-to-space ratio of 1:1.

Utilization means 31 shown in FIG. 1 may be a density indicator, a specific gravity indicator, a process controller or otherwise.

Figure 2:
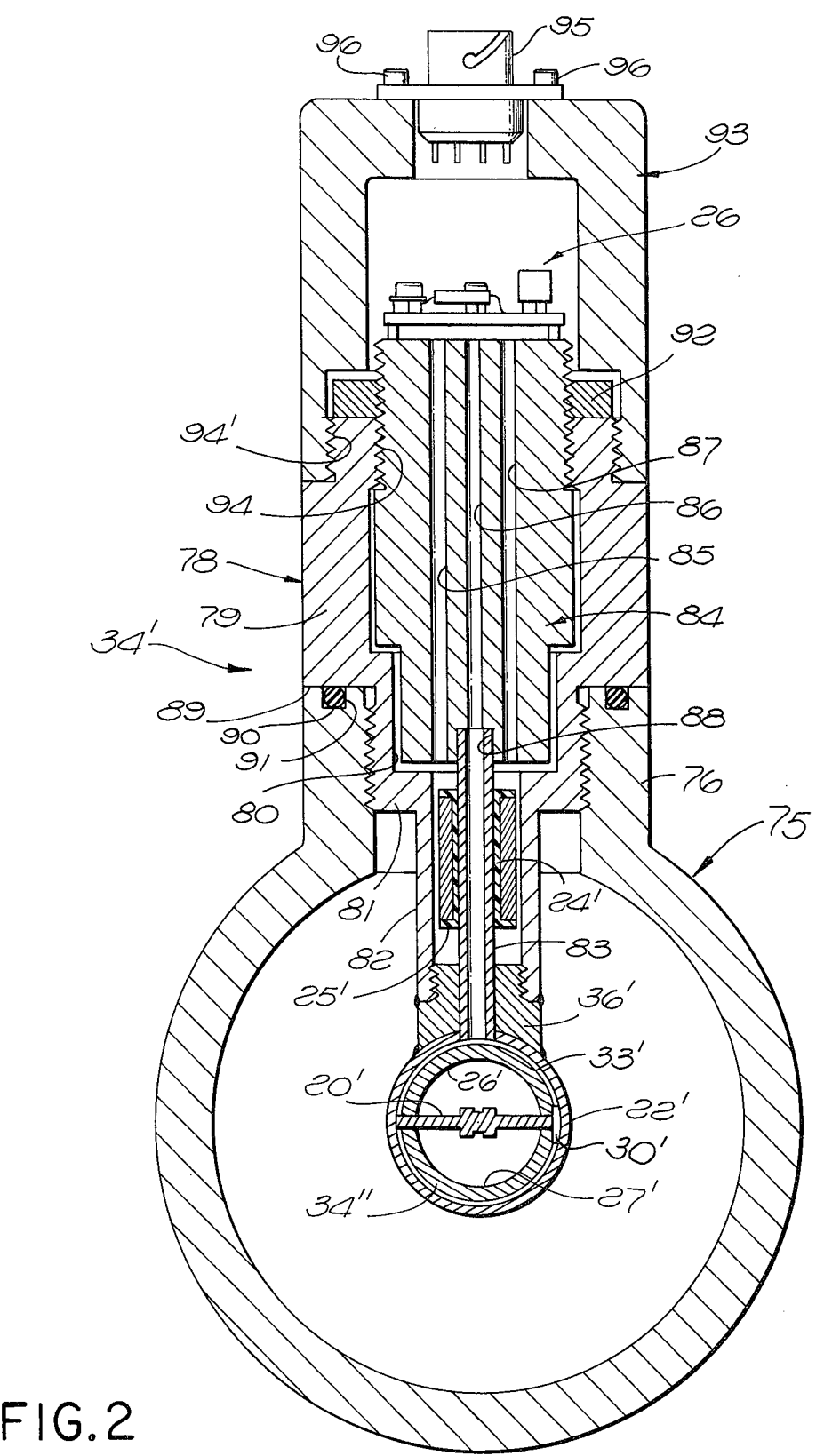
FIG. 2 is a vertical sectional view through a densitometer probe constructed in accordance with the present invention.

The structure of FIGS. 1 and 2 except for vane 20' may be identical to those shown in U.S. Pat. Nos. 3,741,000 and 3,878,374.

Preamplifier 26 shown in FIG. 1 may be conventional.

OPERATION

In the embodiment of the invention shown in FIG. 1, probe 34' and loop circuit 29 provide an electromechanical oscillator which oscillates at a frequency dependent upon the density of the fluid in which vane 20' is immersed. The same is true of the pulse repetition frequency of the square wave voltage applied to the input lead 35 of digital function generator 30.

Digital function generator 30 (which may be described as a digital linearization circuit) may be identical to that shown in said U.S. Pat. No. 3,878,374. So may be loop circuit 29 and utilization means 31. Digital function generator 30 produces a digital output directly proportional to density from the input signal thereto impressed upon the input lead 35 thereto.

Preamplifier 26 shown in FIG. 2 is a differential amplifier and is mounted on a conventional card, if desired. A shield 93 is provided. Preamplifier 26 may be supported inside shield 93.

In FIG. 2, a pipeline is indicated at 75 having a hollow boss 76 in which a probe 34' is located.

Probe 34' has a housing 78 including an upper heavier portion 79, an intermediate portion 80, transverse portion 81 and a hollow portion 82.

All of the portions 79, 80, 81 and 82 are integral with one another.

Parts 22', 26', 27' and 36' may, if desired, be identical to parts 22, 26, 27 and 36, respectively, shown in FIG. 2 of U.S. Pat. No. 3,741,000.

Parts 26' and 27' have grooves 33' and 34" therein. A crystal 30' is shown in FIG. 2.

Boss 36' forms a hollow cylinder or ferrule which has a reduced diameter portion at its upper end to which housing portion 82 is threaded.

A magnetostrictive tube 83 is shown in FIG. 2 that has its lower end slidable through ferrule 36' and cylinder 22'. Tube 83 lies in engagement with an upper portion of the external cylindrical surface of cylinder 26', as before. The lower end of tube 83 is not bonded to the cylinder 26'.

The upper end of tube 83 is press fit into a supporting body 84. Body 84 has three holes 85, 86 and 87 extending completely therethrough in a vertical of axial direction. Body 84 has a counter bore 88 into which tube 83 is press fit, as aforesaid.

The external surface of housing portion 80 is threaded into boss 76. Housing 78 may thus be fixed rigidly relative to pipeline 75. Housing portion 79 has a shoulder 89 which abuts the upper end of boss 76. An O-ring 90 is located in a groove 91 in the upper end of boss 76 to provide a fluid tight seal thereat.

A spool 25' is press fit on tube 83. Spool 25' carries a coil 24'.

The passages 85 and 87 are provided in body 84 for the coil leads. The passage 86 in body 84 aligns with the hole through tube 83 to provide a path through which the crystal leads may be threaded.

It is not critical which particular types of materials are employed for body 84, housing 78 or tube 83. Preferably housing 78 and body 84 are made of a magnetic material such as 416 stainless steel.

The upper end of body 84 is threaded into housing 78 at portion 94. A jam nut 92 holds body 84 in a fixed position relative to housing 78.

Differential amplifier 26 is fixed relative to body 84. An end cap 93 has an internal thread 94' which is threaded externally to housing 78. A conventional electrical connector 95 is fixed to cap 93 by bolts 96. A resilient mounting for connector 95 is thus not required.

In the assembly of the portion of FIG. 2, before end cap 93 is assembled to housing 78, and before jam nut 92 is threaded onto the upper end of body 84, body 84 is turned by hand, i.e. with the fingers, until tube 83 is placed in moderate compression against cylinder 26'. Jam nut 92 is then run down tight against the upper end of housing 78, and cap 93 is threaded thereto.

As stated previously, all structures shown in FIGS. 1 and 2 may be identical to those shown in U.S. Pat. Nos. 3,878,374 and 3,741,000, respectively, except vane 20'. Moreover, probe 34' in both of the FIGS. 1 and 2 may be identical to the probes of said U.S. Pat. Nos. 3,878,374 and 3,741,000 except for the vane 20', and the probe of either patent may be identical to that of the other. For further details of operation, see both of the said patents.

Vane 20' is constructed, assembled and fabricated as described below.

Figure 4:
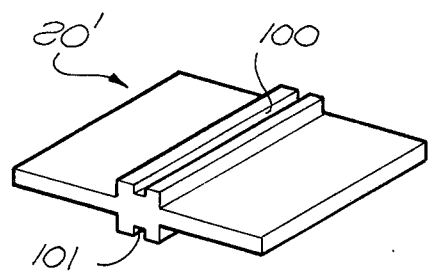
FIG. 4 is a perspective view of the fully fabricated vane shown in FIG. 2.

Vane 20" is cut to the shape as shown in FIG. 4 preferably by a conventional process known as electric discharge machining. Vane 20" is then mounted in the conventional way between half cylinders 26' and 27'. See U.S. Pat. No. 3,677,067. Then, after constructing the entire system of FIG. 1 with vane 20" in place, with a broach or file, notches 100 and 101 are cut the same depth until vane 20' vibrates at a selected frequency in air, and as shown on indicator 31 (FIG. 1).

Figure 3:
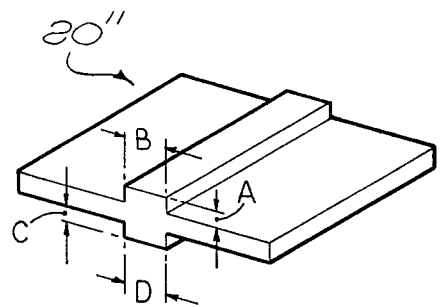
FIG. 3 is a perspective view of a partially fabricated vane shown in FIG. 2.

Dimensions A and B in FIG. 4 are equal to dimensions C and D therein, respectively. Vanes 20" and 20' in FIGS. 3 and 4, respectively, are both symmetrical.

In accordance with the foregoing, a proper calibration for a fluid mixture, compensation for a calibration shift between fluids and a plug-in calibration are made possible by making the vane frequency of all probes the same in the manner described above.

Figure 5:
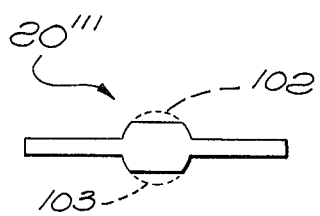
FIG. 5 is a perspective view of an alternative embodiment of the vane of the present invention.

Vane 20''' in FIG. 5 is an alternative which has been filed off at 102 and 103. The embossments may be fixed to or integral (isotropic) with all the respective vanes.

What is claimed is:

1. A vibration densitometer probe, said probe comprising: a substantially fixed structure; a vane; and means to support said vane on said fixed structure, said vane having a symmetrical embossment on each side thereof, said fixed structure including a hollow cylinder having a symmetrical axis, said vane being generally rectangular in plan view defined between a pair of longitudinal edges fixed relative to and inside said cylinder, said vane having a symmetrical axis coincident with said cylinder axis, said embossments being symmetrically fixed relative to said vane on opposite sides of said vane and said coincident cylinder and vane axes.

2. The invention as defined in claim 1, said embossments being spaced from said vane longitudinal edges.

3. The method of manufacturing, said method comprising the steps of: fabricating a plurality of densitometers, a frequency indicator, a plurality of probes, and a vane for each of said probes, each vane having a symmetrical embossment on each side thereof; causing one of said vanes to vibrate, said frequency indicator indicating the frequency of vibration of said one vane; and shaving off the embossment on said one vane until said indicator shows that said one vane is vibrating at a selected frequency.

* * * * *